United States Patent

Chaumont et al.

[11] Patent Number: 5,242,827
[45] Date of Patent: Sep. 7, 1993

[54] APPARATUS FOR THE AUTOMATIC, CONTINUOUS CLEANING OF THE PIPE OF THE SOLAR RECEPTOR OF A PHOTOBIOREACTOR

[75] Inventors: Daniel Chaumont, Venelles; Patrick Ferreira Dos Santos, Aix en Provence; Léopold Sauze, St. Maime, all of France

[73] Assignees: Commissariat a l'Energie Atomique, Paris; Ussi-Ingenierie, Bagneux, both of France

[21] Appl. No.: 858,710

[22] Filed: Mar. 27, 1992

[30] Foreign Application Priority Data

Mar. 28, 1991 [FR] France .................. 91 03781

[51] Int. Cl.⁵ .................. B08B 9/00; C12M 3/00; F16K 51/00
[52] U.S. Cl. .................. 435/287; 435/284; 435/291; 15/3.51; 251/145
[58] Field of Search .............. 435/284, 286, 287, 289, 435/291; 15/3.5, 3.51; 251/129.11, 145, 148

[56] References Cited

U.S. PATENT DOCUMENTS

| | | | |
|---|---|---|---|
| 3,186,014 | 6/1965 | Allen | 15/3.51 |
| 3,288,163 | 11/1966 | Craven | 15/3.51 |
| 4,385,660 | 5/1983 | Koller | 15/3.51 |
| 4,868,123 | 9/1989 | Berson et al. | 435/301 |
| 4,984,629 | 1/1991 | Voith et al. | 15/3.51 |

FOREIGN PATENT DOCUMENTS 2576034 7/1986 France .

*Primary Examiner*—Robert J. Warden
*Assistant Examiner*—T. A. Trembley
*Attorney, Agent, or Firm*—Oblon, Spivak, McClelland, Maier & Neustadt

[57] ABSTRACT

An apparatus for the automatic, continuous cleaning of the pipe of a solar receptor of a photobioreactor also having a carbonator associated with the solar receptor. The solar receptor and the carbonator both being traversed in series in a closed loop by a nutrient medium solution. A branch duct being provided between an outlet and an inlet of the solar receptor to permit a circulation of cleaning balls therebetween. The apparatus including a motorized valve on a vertical portion of the branch duct for bringing about the automatic passage of the balls with the exclusion of the solution, as well as a pivoting sleeve placed in the inlet of the solar receptor, downstream of the junction with the branch duct. The sleeve serving as a support for a controllable manual valve and permitting the introduction or removal of cleaning balls with respect to the pipe. The apparatus also including first and second rod systems each equipped with a regulatable penetrating rod able to stop or permit the passage of the cleaning balls while allowing the circulation of the solution. The first rod system being positioned at the junction of the intake pipe of the carbonator and the branch duct and the second rod system being positioned at the inlet of the solar receptor, immediately downstream of the manual valve.

4 Claims, 4 Drawing Sheets

APPARATUS FOR THE AUTOMATIC, CONTINUOUS CLEANING OF THE PIPE OF THE SOLAR RECEPTOR OF A PHOTOBIOREACTOR

BACKGROUND OF THE INVENTION

1. Field of the Invention

The present invention relates to the field of photobioreactors, i.e. apparatuses permitting the controlled growth of photosynthetic microorganisms (microalgae, etc.).

2. Discussion of the Related Art

Conventionally, photobioreactors have positioned in series in a pipe closed on itself and traversed by a nutrient medium solution, a carbonator and a solar receptor. The carbonator is the point in the circuit where the solution is enriched with carbon dioxide gas and the solar receptor the point in the circuit where the nutrient solution is exposed to solar radiation in order to obtain the transformation of the carbon dioxide gas into biomass. This biochemical reaction corresponds to a photopolymerization of the carbon dioxide gas, which can be represented by the Myers equation:

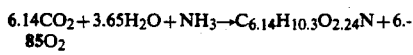

$$6.14CO_2 + 3.65H_2O + NH_3 \rightarrow C_{6.14}H_{10.3}O_{2.24}N + 6.85O_2$$

It is also known that such apparatuses roughly become dirty or contaminated unless special precautions are taken. Thus, adhesions of microalgae occur in a natural manner, particularly on the inner walls of the solar receptor pipes and the extent of this phenamenon is a function of the cultured alga species, as well as the constituent material of the tubes forming the solar receptor and the culturing conditions. In addition, the photosynthesis activity of the algal cells can lead to the appearance of gas pockets within the solar receptor pipes. Such an accumulation of gases leads to a reduction of the culture volume exposed to light and therefore significantly reduces the efficiency of the system. At these gas pockets, it also leads to the drying out of the microalgae and the appearance of a film of dead cells. As a function of the circulation flow rate, which determines the linear velocity of the culture in the tubes, and the type of cultured microorganisms, sedimentation can also occur in the tube. These two effects, adhesion of microalgae and sedimentation, lead to a reduction in the volume of culture exposed to the light; to an evolution of the culture towards a heterogeneous state, because the sedimented cells or the cells fixed to the tube walls escape the continuous culture dilution rate; and to an increase of contamination risks as a result of the development of bacteria and/or protozoa, which develop in the absence of light or at the expense of the dead cells.

It is known in general terms for the permanent cleaning of the interior of pipes of such apparatuses to introduce into the pipes plastic material balls, which are therefore circulated with the culture medium and permanently ensure an agitation of the nutrient medium, together with a cleaning of the tubes as a result of the balls rubbing on their walls.

In order to be effective, this cleaning must be continuous and automatic. Moreover, the use of pumps for circulating the nutrient solution in the tubes and the presence of measuring probes, makes it necessary to limit the cleaning by the balls to the solar receptor only, while excluding the carbonator. Therefore, a cleaning apparatus for such a photobioreactor must contain a system for recycling the balls between the solar receptor inlet and outlet.

The closest prior art in this field is represented by French patent 2,576,034, which describes two constructions for ensuring such a recycling. A description will be given hereinafter with reference to FIGS. 1 and 2, of these two prior art constructions described in the aforementioned patent relating to the circulation of cleaning balls in the solar receptor only. FIGS. 1 and 2 show the photobioreactor with its pipe looped onto itself and incorporating the solar receptor 2 exposed to the radiation 5, as well as the carbonator 6 in series with the aforementioned loop. A pump 10 circulates the liquid nutrient medium throughout the pipe.

In the first construction according to FIG. 1, which is a manual operating mode, use is made of a ball recovery basket 12 having two compartments 14 and 16. The compartment 14 is installed on the outward branch of the photobioreactor circuit and the compartment 16 is installed on the return branch of the circuit. The basket 12 is installed so as to pivot by 180°, so that on turning the basket, the compartments 14 and 16 are inverted. During the operation of the installation, the balls are held in the compartment 16 and accumulate there. When the compartment 16 is full, the basket 12 is pivoted by 180° so as to reverse the position of the compartments 14 and 16. The balls in compartment 16 can then be introduced into the circuit by the circulation of the fluid. The reversal of these two baskets 14 and 16 can take place without stopping the circulation of the culture as a result of not shown pipe branches. However, this system involves the opening of the general pipe and consequently the contacting for a certain time of the culture with the exterior. This leads to unacceptable contamination risks of a biological nature such as microorganisms being introduced into the duct.

In the construction according to FIG. 2, there is a specific separation between the solar receptor 2 and the remaining pipe branch in which is located the carbonator 6 by having a branch 7 between the solar receptor inlet and outlet in the following way. A stop grating 18 for the balls is installed on the return branch of the photobioreactor. A special pump 20 for the circulation of the balls is branched onto the outward and return branches of the circuit upstream of the grating 18 with respect to the suspension flow direction. The pump 20 is e.g. a vortex effect pump. In this case, there is no need for the main circuit pump to be a pump which permits the circulation of the balls, so that any random pump type can be used. In view of the fact that the deoxygenating carbonator 6 is not traversed by the balls, because it is not located on the circuit of the pump 20, there is no need for it to allow the circulation of the balls and it is consequently installed directly on the circuit.

In this case, the ball recycling pump 20 operates continuously so that, at the same time as the balls, a significant part of the culture passes directly into the solar receptor without being carbonated. This constitutes a major disadvantage with respect to the efficiency of the photosynthesis reaction and it has also been found that the use of pumps on the solar receptor circuit was very prejudicial to the cells of certain species of microalgae.

For all the above reasons, neither of the prior art arrangements permitting the limitation of the circulation of the balls to the solar receptor functions in a satisfactory manner.

SUMMARY OF THE INVENTION

The present invention relates to an apparatus for the automatic, continuous cleaning of the pipe of the solar receptor of a photobioreactor which, with the aid of means having a simple and effective construction, to obviate the disadvantages of the prior art referred to hereinbefore.

The automatic, continuous cleaning apparatus according to the invention is characterized in that it comprises: on a vertical portion of the branch duct, a motorized valve bringing about the automatic passage of the balls, with the exclusion of the solution; a pivoting sleeve placed in the intake pipe of the solar receptor, downstream of the junction with the branch duct, the sleeve serving as a support for a manual valve orientable with respect to gravity and permitting the introduction or removal of cleaning balls with respect to the pipe; two rod systems, each equipped with a regulatable penetrating rod able to stop or permit the passage of the cleaning balls while allowing the circulation of the solution and positioned a) for the first, at the junction of the intake pipe, the carbonator and the branch duct,
b) for the second, in the intake pipe of the solar receptor, immediately downstream of the orientable manual valve.

As will be shown in greater detail hereinafter in connection with a description of an embodiment of the apparatus, this apparatus makes it possible to completely obviate the deficiencies of the prior art by using a structure branched to the inlet of the solar receptor, simultaneously valves of a particular type, whereof one is manual and the other automatic, but which are able in both cases to only allow the passage of the balls, while excluding the liquid solution. These valves, used in conjunction with rods passing through rod systems fixed to the pipe wall and which make it possible to open and close the passage to the balls while permitting that of the solution, lead to an apparatus entirely meeting practical needs.

According to a first and very important feature of the invention, the motorized valve and the orientable manual valve have a spherical cap in which there is a blind hole, whose dimensions are slightly larger than those of a ball.

This feature according to which the spherical cap has a cup shape making it possible to house a ball allows, simply by turning by 180° to pass the ball through the valve, while maintaining the necessary seal with respect to the liquid nutrient solution.

According to another feature of the invention, the motorized valve is equipped with a ball presence detector which, as soon as a ball drops by gravity into the blind hole which is turned upwards in the waiting position, controls the rotation of the cap by 180° in order to bring the opening of the blind hole towards the bottom and release the ball by gravity into the branch duct, followed by a further 180° rotation to return the valve to the waiting position for the next ball with the blind hole open to the top.

The placing of this motorized valve in a vertical pipe surmounting the intake duct for the culture in the solar receptor permits, when operating under gravity, for the ball to be received in its housing when the blind hole is oriented towards the upstream side of the vertical pipe and introduce it into the solar receptor when the same blind hole, following a 180° rotation of the spherical cap, is turned towards the bottom of the branch duct. Following the passage of a ball, the spherical cap is again rotated by 180° in order to reassume its initial position, the blind hole being oriented towards the top waiting for the following ball.

According to another feature of the invention, the pivoting sleeve is placed in a first position, bringing the manual valve into a vertical position above the intake duct in the solar receptor, for the introduction of a ball into the pipe, and into a second position 180° from the first and which brings the manual valve into a vertical position below the intake pipe in the solar receptor, for the extraction of a ball from the pipe.

The second rod system positioned immediately downstream of the orientable manual valve is in the open position for the balls and the blind hole of the orientable manual valve is directed upwards, so that a new ball can be introduced into it, which by rotation by 180° of the spherical cap, is made by gravity to drop into the intake pipe of the solar receptor, where it is carried along by the stream of nutrient liquid.

However, if the pivoting sleeve is turned in such a way that the orientable manual valve is below the pipe with the blind hole directed towards the intake pipe of the solar receptor, it is merely necessary to close the second rod system for the first ball to arrive and drop by gravity into the spherical cap. It is then necessary to pivot the cap by 180° to make the ball drop towards the outside and permit its extraction from the system.

Figure 1:
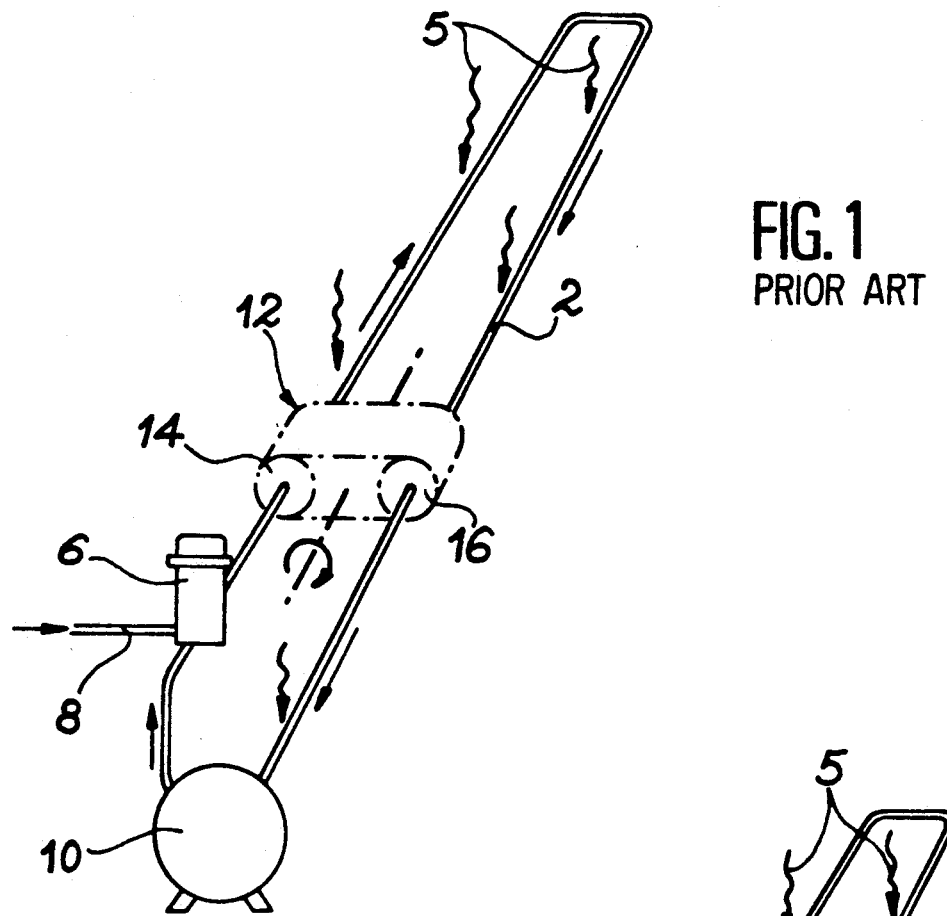
FIGS. 1-2 An overall view of two prior art constructions for recycling cleaning balls, in a solar receptor only, of a photobioreactor.
Figure 2:
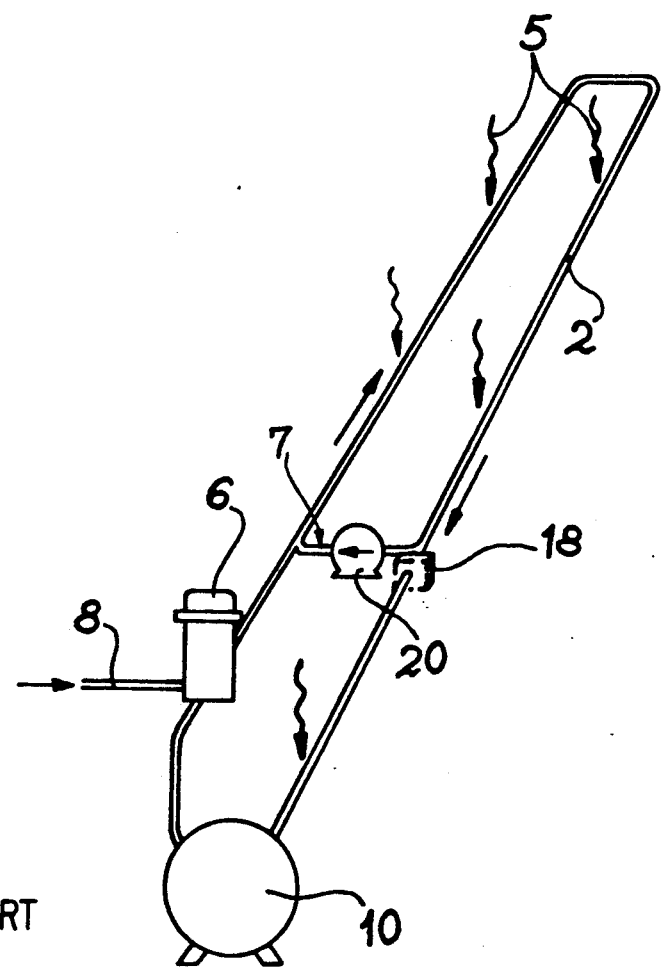
Figure 3:
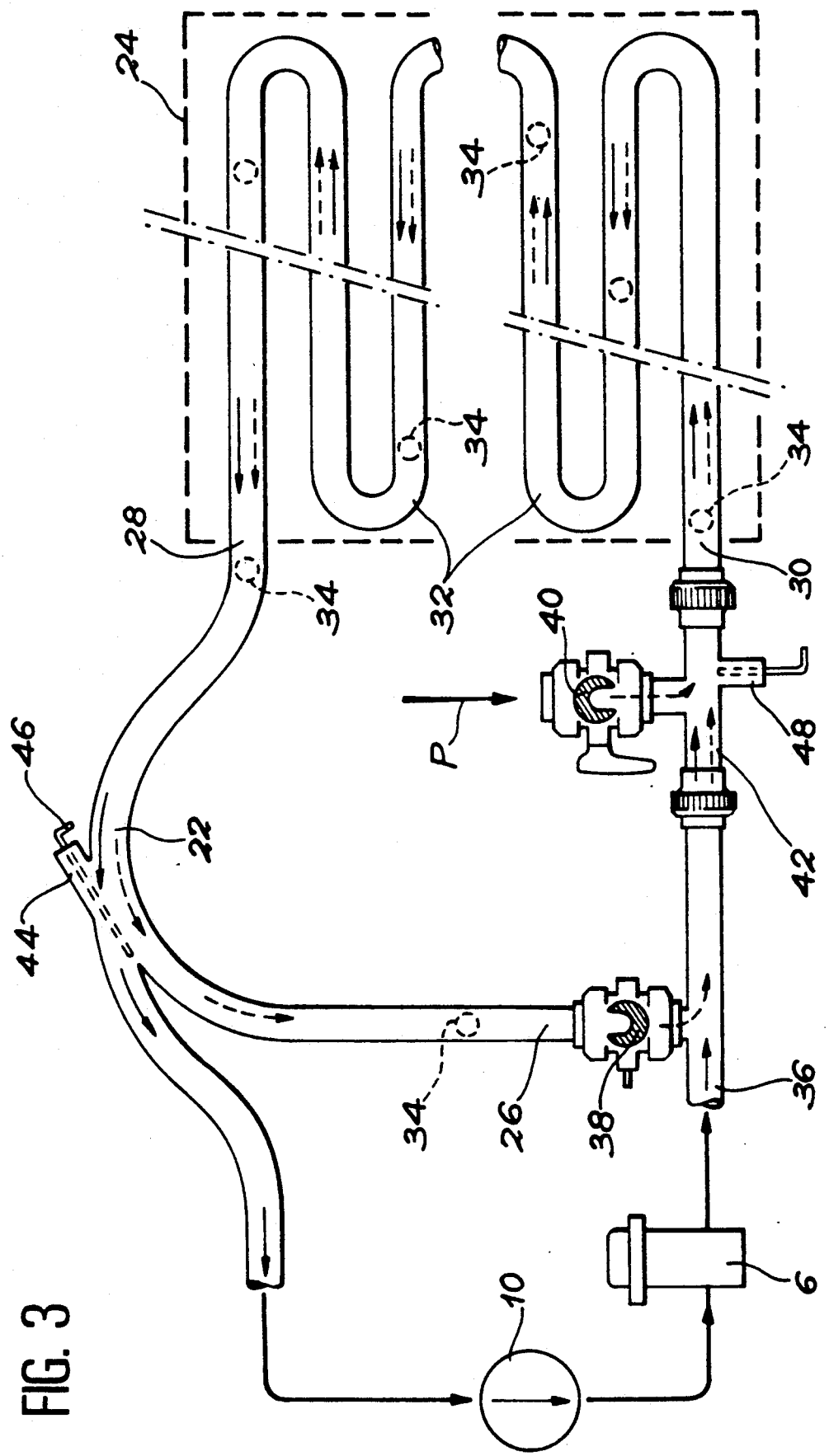

The invention is described in greater detail hereinafter relative to a non-limitative embodiment of an automatic cleaning apparatus with reference to the attached FIGS. 3 to 5, wherein show:

FIG. 3 An overall view of a photobioreactor according to the invention.

Figure 4:
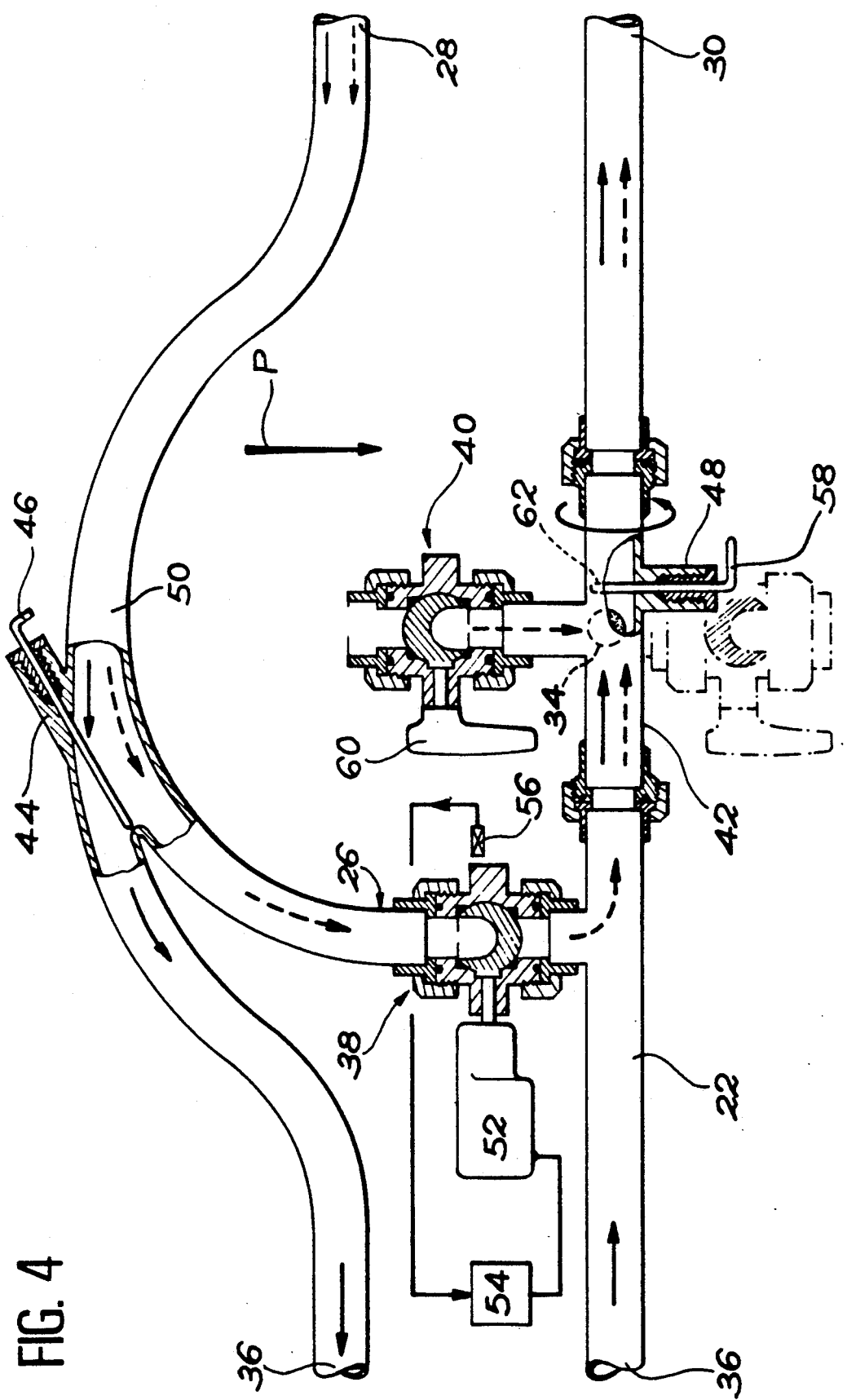

FIG. 4 A more detailed diagram of valve and glove finger systems installed on the apparatus in the vicinity of the branch duct at the inlet of the solar receptor.

Figure 5:
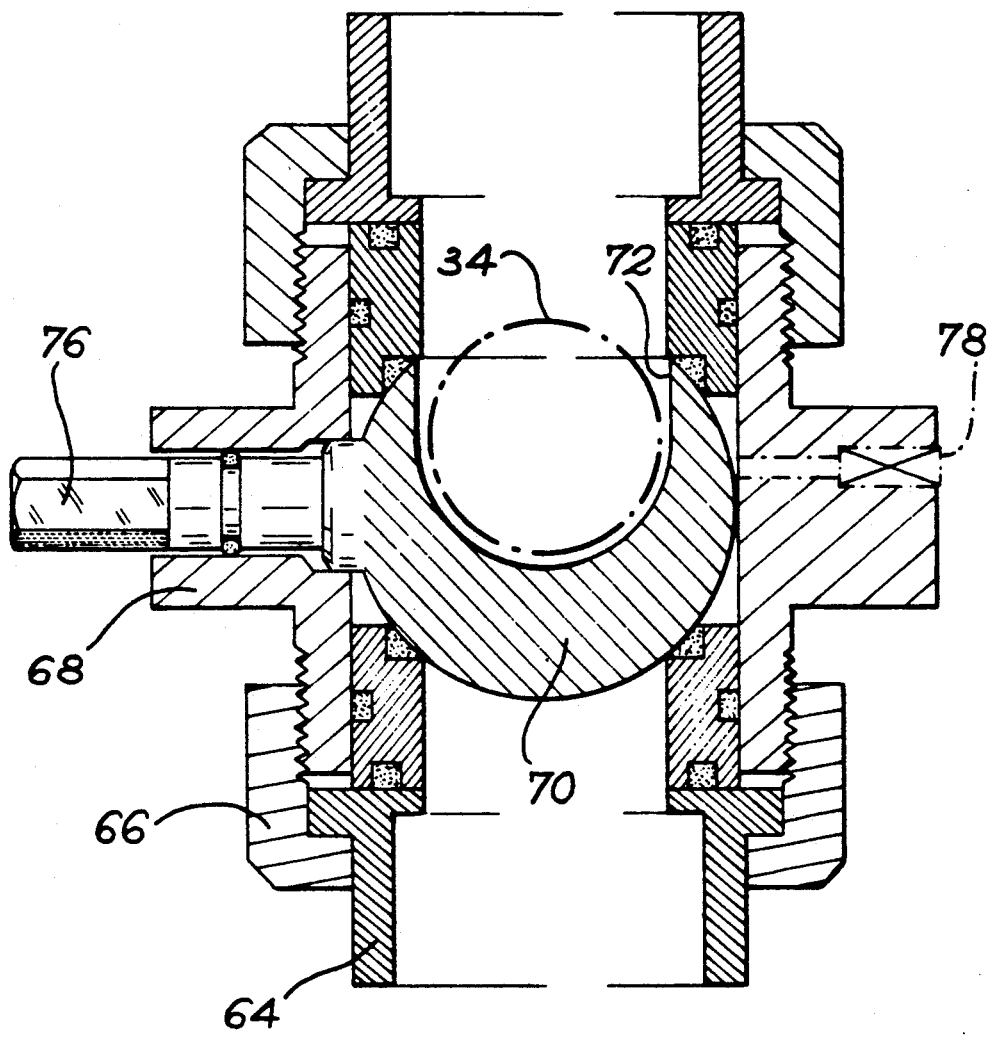

FIG. 5 In detail the construction of one of the spherical cap valves of FIG. 4.

DESCRIPTION OF THE PREFERRED EMBODIMENTS

FIG. 3 diagrammatically shows in plan view a photobioreactor, whose pipe 22 is in closed loop form and traverses the solar receptor 24 and the circuit of the carbonator of the culture medium incorporating the actual carbonator 6 and the pump 10, as well as the branch duct 26, which connects the outlet 28 of the solar receptor 24 to its inlet 30.

The solar receptor 24 is constituted by a series of loops 32 effected by the pipe 22 and which are by definition exposed to the solar radiation in order to enable the microalgae cultured in the nutrient medium and which pass through the same to undergo the chlorophyll-containing photosynthesis reaction.

In FIG. 3, the circulation path of the liquid nutrient medium is represented by continuous line arrows, whereas the circulation path of the balls is indicated by dotted line arrows. In this embodiment according to the invention, the different balls such as 34 only traverse the solar receptor 24, the carbonator circuit or path 36 only being traversed by the liquid nutrient solution. From this standpoint it is particularly interesting to note that the pump 10, which causes the movement of the solution throughout the installation is located on the path 36, i.e. no ball passes through it. This particular feature leading to the advantages of the apparatus described hereinbefore is made possible by the presence on the branch 26 or around the same, of two valves having a spherical cap and provided with a blind hole in the form of a cup, whereof the first valve 38 only permits the passage of the balls and whereof the second valve 40 is used for introducing or extracting clean balls or which are intended for cleaning. The satisfactory operation of these valves 38 and 40 means that the first valve is located on a vertical pipe portion with the gravity direction indicated by an arrow P, while the second valve is located on a pivoting sleeve 42 making it possible to orient it vertically with the opening of the spherical cap turned either upwards or downwards.

According to the invention, these two valves are completed by the presence of two rod systems, each having a regulatable, penetrating rod and which makes it possible either to stop, or to allow the passage of the cleaning balls, while permitting the free circulation of the solution. The first of these rod systems 44 is located at the junction of the pipe of the carbonator 6 and the branch duct 26. The penetrating rod 46 of the rod system 44 can be manually handled from the outside and permits the stopping of the balls 34 by preventing their entry into the circuit of the carbonator 6 when the rod 46 is inserted, while permitting the passage of the nutrient solution. The second rod system 48 is located on the pivoting sleeve 42, immediately downstream of the orientable manual valve 40 and has a movable rod 58. In a particularly interesting embodiment of the invention, the valve 38 is motorized and, as will be explained hereinafter during the description of FIG. 4, is automatically controlled by a ball presence detection cell in the valve 38.

In the embodiment of FIG. 3, the solar receptor 24 is shown as being constituted by a certain number of U-tubes 32, in which circulates several balls 34 distributed at as regular as possible intervals within the pipe. Obviously, this is only an example and the solar receptor pipe could have any other appropriate shape and the number of balls used is dependent on the amount of dirtying of the installation, the automatic cleaning apparatus according to the invention, in an extreme case, being able to operate with a single ball. When operating with a single ball, it is important, bearing in mind the revolution time of the balls in the solar receptor 24, to keep the opening of the blind hole of the spherical cap of the valve 38 directed downwards so as to prevent, during the time, the dirtying and in particular sedimentation within the blind hole of the spherical cap. The opening of the blind hole will not be reoriented upwards to receive the ball until after a time lag corresponding to the duration of the circulation of the ball in the solar receptor 24, or on the basis of the instruction from a detection cell, e.g. placed at the solar receptor outlet.

On referring to FIG. 4, a description will now be given of that part of the photobioreactor of FIG. 3 in which are located the means according to the invention, i.e. the part located around its branch 26. FIG. 4 shows the same element as in FIG. 3, so that the same reference numerals are used for them.

With respect to the different pipes or ducts, it is possible to see the branch duct 26 and on the general circulation duct for the nutrient medium, the part 36 which corresponds to the carbonation system circuit, and at 28 and 30 respectively the outlet and inlet of the solar receptor 24, which is not shown in FIG. 4.

As in FIG. 3, the apparatus is not randomly positioned with respect to gravity, which is indicated by the vector P and, at the solar receptor outlet, the duct 28 forms a loop 50 located in a vertical plane above the pipe 22 to permit the dropping or introduction by gravity of balls into the valve 38.

In FIG. 4, the valve 38 is operated by a motor 52, which makes the valve rotate on each occasion by 180° under the influence of a control 54 receiving information from a ball detection cell 56 indicating the presence of a ball in the blind hole of the spherical cap of the valve 38. The construction and operation of the valve 38, as well as the valve 40 will be better understood from the description given relative to FIG. 5.

With reference to FIG. 5, a more detailed description will be given of the construction of one of the manual or motorized valves used in the invention and designated 38 and 40 in FIG. 4. Such a valve fixed to the duct 64 by a nut 66 has a valve body 68 serving as a housing for the cup-shaped spherical cap 70 made by hollowing out a blind hole 72 in the cap 70. This blind hole directed along the axis of the pipe 64 in the open position gives the valve cap its characteristic cup shape which, when oriented in the manner shown in FIG. 5, can serve as a receptacle for a ball arriving by the duct 64, whereas it can also completely stop both the circulation of the balls and the liquid solution arriving at 64 when, as a result of a 180° rotation applied by a not shown motor to the control shaft 76, it presents the convex part of the cap 70 to the pipe 64. FIG. 5 also shows the insertion recess 78 for the ball presence detection cell 56 in the cup-shaped cap 70.

According to the invention, the manual control spherical cap valve 40 is mounted on the pivoting sleeve 42 placed in the intake pipe 30 of the solar receptor. This sleeve makes it possible to manually rotate the valve 40 to bring it into the vertical position, either above the pipe 22 as is the case in FIG. 4, or below it.

The rod system 44 has its penetrating rod 46 in the insertion position, while the balls circulate in the loop 50, where it has the effect of allowing the nutrient solution to pass to the intake 36 of the carbonation system, while permitting the balls to follow the vertical downward part of the loop 26. As stated, the rod 46 is positioned immediately downstream of the manual valve 40 on the sleeve 42 at the inlet into the solar receptor.

Under these conditions, the apparatus of FIG. 4 functions in the following way. In the waiting position, i.e. for the time separating the arrival of two consecutive balls in the pipe 28, the motorized valve 38 has the blind hole of its spherical cap directed upwards. Correlatively and in general terms permanently, the rod system 44 has its penetrating rod 46 inserted in the junction separating the loop 50 from the carbonation system intake, thus making the balls entering the loop 50 pass into the downward part 26 and then drop by gravity into the spherical cap of the valve 38. Conversely and as stated, the nutrient medium solution containing the algal culture can freely pass from the loop 50 to the carbonation system intake 36. As soon as a ball has dropped into the blind hole of the valve 38, it is detected by a ball detection cell 56 and a signal indicative of the presence of a cleaning ball in the blind hole of the valve 38 and an information is transmitted to the control 54 of the motor 52, which then carries out a half-turn downwards. In this position, the orifice of the blind hole is directed downwards with respect to gravity and the ball can pass freely into the pipe 30, where it is carried along by the liquid nutrient medium from the carbonation system intake 36. At this stage, the absence of the ball in the spherical cap of the valve 38 is noted by the detector 56 and a new instruction is given by the control 54 to the motor 52, which again carries out a 180° rotation in one or other direction in order to place the spherical cap of the valve 38 in the waiting position for receiving the following ball.

The manual control spherical cap valve 40 permits the introduction and extraction of balls with respect to the photobioreactor circuit.

The introduction operations take place in the following way. With the blind hole of the cap directed upwards, a new ball is introduced at the top of the valve 40. Correlatively, the rod 58 of the rod system 48 is manually drawn downwards, thus freeing the circulation of a ball into the pivoting sleeve 42 and the cap of the valve 40 is then manually turned by 180° with the aid of the handle 60. The thus freed ball drops by gravity into the pivoting sleeve 42 and is carried along in the general photobioreactor circulation 30.

For the operations of extracting a dirty ball, the sleeve 42 is rotated by 180° with respect to FIG. 4 in order to place the valve 40 vertically below the sleeve 42. The rod 58 is then inserted in order to stop the possible advance of the next ball into the solar receptor inlet 30 and the valve 40 is operated manually by the handle 60, so that the blind hole of its cap is directed upwards. Under these conditions, as soon as the following ball appears in the pipe 26 and then in the sleeve 42, it is blocked by the rod 58 in the position designated 62 in FIG. 4 and then drops by gravity into the valve 40, from where it can finally be extracted by the 180° rotation imparted to the handle 60, which places the orifice of the blind bore of the spherical cap in the downwards position. It then drops by gravity to the exterior, where it only has to be collected. The passage is then freed for the next balls by pulling the penetrating rod 58 of the rod system 48 in order to bring them into the position which they occupy in FIG. 4. In order to prevent any biomass sedimentation, the valve 40 is returned to the waiting position, i.e. above the sleeve 42.

The ball presence or absence detection system 56 can obviously be of a random nature. In the case where it is constituted by a photoelectric cell, the valve body and the cup-shaped spherical cap must necessarily be transparent and they can be made from a plastics material, such as e.g. polymethacrylate.

However, if it is a question of a magnetic or electromagnetic detection, this implies each ball having a spherical fitting.

In other embodiments of the invention which can be used in special cases, the recycling of the balls can take place as follows:
automatically (detection of the passage of balls by photoelectric or electromagnetic cells);
manually (electrical pulses permitting the sought positioning of the cup of the motorized valve);
semiautomatically (in the case where the detection systems may be inoperative e.g. due to excessive cellular concentrations or an excessive tube diameter). In this case, the adequate positioning of the cup of the motorized valve is determined by two time lags. A first time lag determines the time during which the cup remains in the inverted position (opening upwards). Its duration is a function of the length of the tube to be cleaned and the culture circulation flow rate. At the end thereof, the cup position is reversed. A second time lag determines the time during which the cup remains in this position. It permits a good positioning of the ball in the cup.

The cleaning apparatus according to the invention:
permits an automatic, continuous recycling of the balls in the tubes;
requires no pump and consequently does not damage the algal cells; does not involve the stopping of the culture circulation, or the opening of the system and consequently limits contamination risks;
leads to a very small amount of culture being reintroduced at the same time as the ball at the solar receptor inlet and which is consequently not carbonated (volume below 1/10000 of the total culture volume).

We claim:

1. An apparatus for the automatic, continuous cleaning of the pipes of a solar receptor of a photobioreactor and a carbonator associated with the solar receptor, the solar receptor having an outlet and an inlet and both the solar receptor and carbonator being traversed in series in a closed loop by a nutrient medium solution, a branch duct being provided between the outlet and inlet of the solar receptor to permit a circulation of cleaning balls therebetween, wherein the apparatus comprises:

a motorized valve positioned on a vertical portion of a branch duct provided between an outlet and inlet of a solar receptor for providing an automatic passage of the cleaning balls without the passage of a nutrient medium solution;

a pivoting sleeve placed in the inlet of the solar receptor and located downstream of the branch duct with respect to the circulation of the cleaning balls through the branch duct, said pivoting sleeve serving as a support for a controllable manual valve and permitting the introduction or a removal of cleaning balls from a closed loop formed by the solar receptor and a carbonator; and first and second rod systems, each of said first and second rod systems being equipped with a regulatable penetrating rod for stopping or permitting the passage of the cleaning balls while allowing the circulation of a nutrient medium solution, the first rod system being positioned at a junction of an intake pipe of the carbonator and the branch duct, and the second rod system being positioned at the inlet of the solar receptor immediately downstream of the controllable manual valve with respect to the circulation of the cleaning balls through the manual valve.

2. The automatic cleaning apparatus according claim 1, wherein the motorized valve and the controllable manual valve comprise a spherical cap having an opening with dimensions slightly larger than those of a cleaning ball.

3. The automatic cleaning apparatus according to claim 2, wherein the motorized valve is equipped with a cleaning ball presence detector, such that when the opening of the spherical cap is turned vertically upward in a waiting position, a cleaning ball drops by gravity into the opening of the spherical cap, and the cleaning ball presence detector controls the rotation of the spherical cap by 180° in order to direct the opening of the spherical cap vertically downward to release the cleaning ball by gravity into the closed loop and then a further 180° rotation in order to again bring the spherical cap to the waiting position for receiving the next cleaning ball.

4. The automatic cleaning apparatus according to claim 2, wherein the pivoting sleeve comprises means for permitting the rotation of the pivoting sleeve from a first position in which the controllable manual valve is in a vertical position above the inlet of the solar receptor for allowing the introduction of a cleaning ball into said closed loop, to a second position 180° from the first position for extracting a cleaning ball from the closed loop.

* * * * *